US012440264B2

(12) United States Patent
Segit et al.

(10) Patent No.: US 12,440,264 B2
(45) Date of Patent: Oct. 14, 2025

(54) LARGE AREA HEMOSTASIS WITH VESSEL SEALING

(71) Applicant: Medtronic Advanced Energy LLC, Minneapolis, MN (US)

(72) Inventors: Alexander J. Segit, Portsmouth, NH (US); Steven Ek, Portsmouth, NH (US); James E. Dunning, Boulder, CO (US); Brian Lane, Virginia Beach, VA (US); Erin E. Wehrly, Longmont, CO (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 976 days.

(21) Appl. No.: 17/348,690

(22) Filed: Jun. 15, 2021

(65) Prior Publication Data

US 2022/0395314 A1 Dec. 15, 2022

(51) Int. Cl.

*A61B 18/14* (2006.01)
*A61B 18/00* (2006.01)

(52) U.S. Cl.

CPC .. *A61B 18/1445* (2013.01); *A61B 2018/0063* (2013.01); *A61B 2218/002* (2013.01)

(58) Field of Classification Search

CPC ........ A61B 18/1445; A61B 2018/0063; A61B 2218/002; A61B 2018/145
See application file for complete search history.

(56) References Cited

U.S. PATENT DOCUMENTS

2007/0208336 A1* 9/2007 Kim .................. A61B 18/1492 606/41
2019/0133674 A1* 5/2019 Singh ................. A61B 18/1442
2021/0205003 A1* 7/2021 Krastins ............. A61B 18/1445

* cited by examiner

*Primary Examiner* — Linda C Dvorak
*Assistant Examiner* — Ryan T Clark
(74) *Attorney, Agent, or Firm* — Husch Blackwell LLP

(57) ABSTRACT

Tools, systems, and methods described herein provide multiple treatments with a reduced number of tools. A single tool as described herein can be used to provide both clamping and sealing treatment modes.

20 Claims, 8 Drawing Sheets

LARGE AREA HEMOSTASIS WITH VESSEL SEALING

FIELD

The present disclosure relates generally to the field of surgical instruments. In particular, the disclosure relates to a multi-function surgical device capable of clamping and sealing for different applications without retracting or replacing the tool.

BACKGROUND

During a surgical procedure, multiple different processes can be carried out at different times that each require specialized equipment. Electrosurgery, for example, typically uses at least one tool designed for application of high-frequency electrical current (e.g., about 200 kHz to about 3.3 MHz), above the range that will cause nerve or muscle stimulation. At different times, a surgeon or other medical professional may be cutting, clamping, sealing (e.g., by application of energy or by application of materials), or applying various therapies. Each of these processes may be performed by a particular tool or set of tools that are specialized for that particular task.

Surgical instruments such as electrosurgical forceps are commonly used in open and endoscopic surgical procedures to treat tissue, such as by coagulating, cauterizing, cutting, or sealing tissue. The combination of mechanical clamping force and electrosurgical energy has been demonstrated to facilitate treating tissue and, specifically, sealing tissue. With respect to mechanical clamping pressure for tissue sealing, for example, it has been found that pressures within the range of about 3 kg/cm$^2$ to about 16 kg/cm$^2$ help ensure formation of effective and consistent tissue seals. Other pressures within or outside this range may be utilized for treating tissue in a different manner and/or for other purposes.

Small Vessel Sealing: LIGASURE® vessel sealing instruments are commercially available from the Applicant and are designed to seal small vessels. By a combination of compression pressure and bipolar radiofrequency (RF) energy, such instruments apply pressure and energy to denature the proteins in the collagen and elastin and allow them to fuse together the opposing layer of denatured proteins (sometimes referred to as "poaching" the treatment area). These instruments are effective in sealing small vessels up to 7 mm in diameter. LIGASURE® in combination with a clamp crushing technique has resulted in lower blood loss and faster transection than previous solutions.

Large Vessel Clamping and Sealing. Larger vessels are often clamped by use of forceps (e.g., bipolar forceps, electroscopic, coagulation forceps, or laparoscopic forceps) or clamps. These devices can be, for example, stainless steel or titanium and either unpowered or powered for use in electrosurgery. Such forceps or clamps are often two-pronged devices, where the prongs can be manually pressed together by the operator to provide compression at the tips where those prongs meet. Electrical sealing can be provided by forceps, or for some large vessels other sealing mechanisms such as stitches, chemical treatments, or the like can be used.

As a general matter, solutions for large vessel clamping and/or sealing are ineffective in treating small vessels. Similarly, devices for treating smaller vessels by poaching will not be effective on larger vessels. These two types of types of tools are currently therefore used separately and as needed throughout a procedure.

SUMMARY

According to embodiments described herein, an improved clamping and sealing system and methods for manufacture and use thereof are provided.

According to an embodiment, a tool is provided that includes a handle at a proximal end, a pair of tips arranged at a distal end opposite the proximal end, each of the pair of tips having a corresponding fluid delivery aperture. A fluid supply is coupled to each of the delivery apertures to provide a fluid thereto, and an electrical controller configured to provide electrical power to each of the pair of tips. A mechanical controller is configured to move the pair of tips relative to one another between a closed configuration and an open configuration.

The handle can include a controller for moving the pair of tips. Each tip of the pair of tips can extend parallel to the other tip of the pair of tips. The mechanical controller can be configured to maintain the pair of tips parallel to one another in both the open configuration and the closed configuration. Each tip of the pair of tips can include a flat portion, and the flat portions of the pair of tips are facing one another in both the open configuration and the closed configuration. The delivery apertures can each be arranged on the flat portions, or opposite the flat portions. The flat portion of each of the pair of tips can include a flange extending from each of the tips. The tool can include a housing having a slot, wherein the pair of tips extend from the slot.

According to another embodiment, a method for providing multiple treatment modes with a single device is provided. The method includes providing a device including a handle at a proximal end, a pair of tips arranged at a distal end opposite the proximal end, each of the pair of tips having a corresponding fluid delivery aperture, a fluid supply coupled to each of the delivery apertures to provide a fluid thereto, an electrical controller configured to provide electrical power to each of the pair of tips, and a mechanical controller configured to move the pair of tips relative to one another between a closed configuration and an open configuration. The method further includes providing the fluid from the fluid supply at each of the delivery apertures, providing an electrical treatment via the pair of tips to provide a sealing treatment function, and moving the pair of tips from the open configuration to the closed configuration to provide a clamping treatment function.

In embodiments, providing the fluid from the fluid supply can occur simultaneously with providing the electrical treatment. Providing the fluid from the fluid supply, providing the electrical treatment, and providing the clamping treatment can all occur simultaneously in some embodiments. The handle can include a controller for moving the pair of tips. Each tip of the pair of tips can extend parallel to the other tip of the pair of tips. The mechanical controller can be configured to maintain the pair of tips parallel to one another in both the open configuration and the closed configuration. Each tip of the pair of tips can include a flat portion. The flat portions of the pair of tips can be facing one another in both the open configuration and the closed configuration. The delivery apertures can each be arranged on the flat portions, or can each be arranged opposite the flat portions. The flat portion of each of the pair of tips can include a flange extending from each of the tips. The device can have a housing defining a slot, wherein the pair of tips extend from the slot.

The details of one or more aspects of the disclosure are set forth in the accompanying drawings and the description below. Other features, objects, and advantages of the techniques described in this disclosure will be apparent from the description and drawings, and from the claims.

Figure 1:
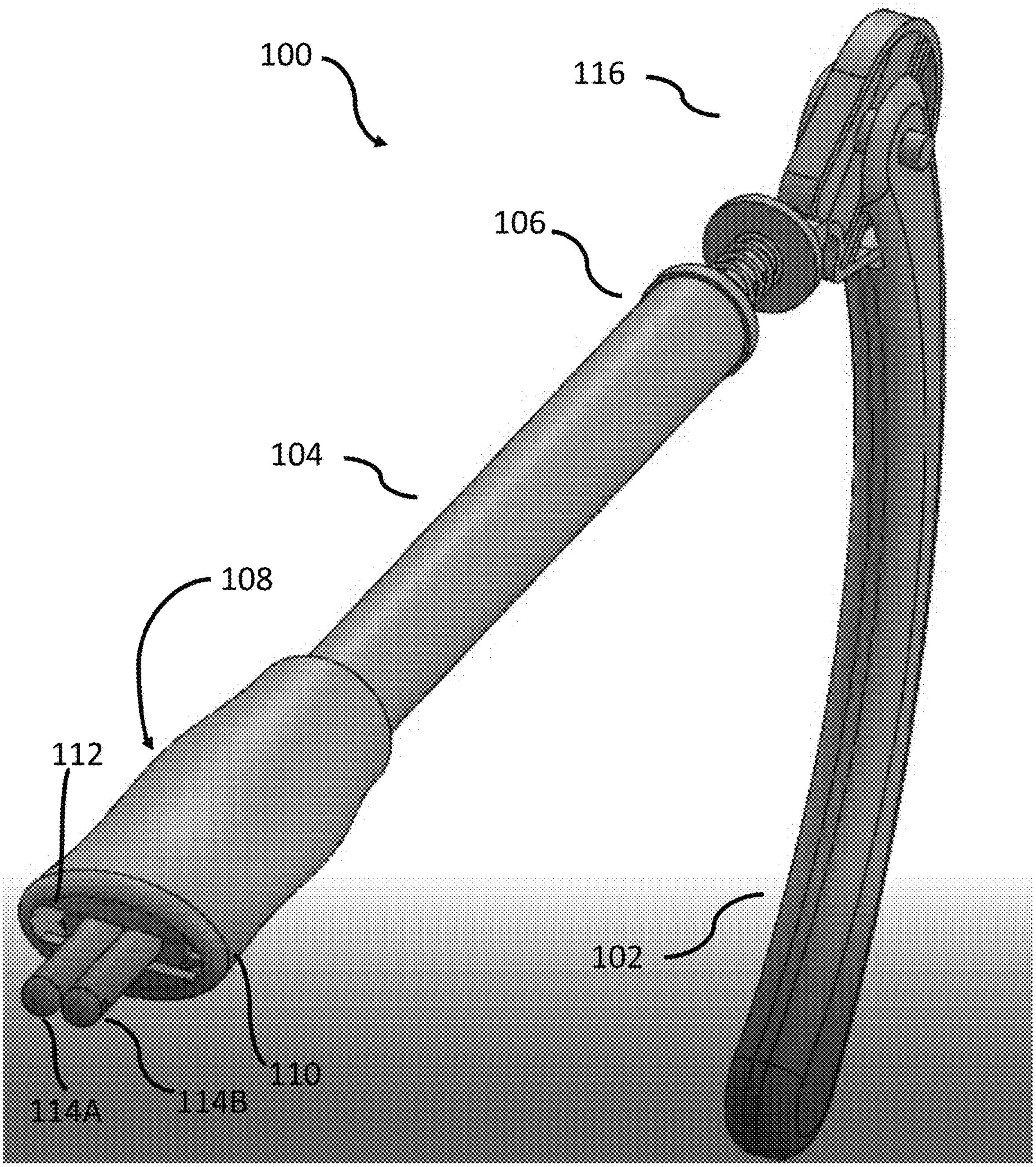
FIG. 1 is a perspective view of a device according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

As a general matter, reducing the number of tools that are used simultaneously is beneficial because each tool will obstruct access in some way, or require a larger incision that would otherwise be required to provide access for the other tools needed to perform the procedure. One solution to this problem is to change specialized tools throughout the procedure such that there are a limited number involved in the procedure at any given time. Changing tools, however, is a process that can present its own challenges.

Some tools (such as those used for clamping) must remain in place during parts of a procedure. Electrosurgical forceps typically include a pair of jaw members that can be manipulated to grasp targeted tissue. The jaw members may be used in conjunction with a knife or an electrical cutting mechanism for cutting or transecting tissue. During complicated surgical procedures, e.g., hepatic transection or resection, additional surgical instruments may be used along with a surgical forceps to supplement or replace specific functions of the forceps, each requiring a tool change or a larger incision.

In one example, a hip replacement procedure, a procedure may involve cutting to reach the target area, and the cutting can pass through both areas with small blood vessels and areas with larger blood vessels. Use of small-vessel treatment electrosurgery devices (e.g., AQUAMANTYS® devices) can be essential for poaching or sealing the smaller vessels. Meanwhile, clamping can be essential simultaneously with the need to seal these smaller vessels.

As described herein, use of a single device provides clamping and small-vessel sealing without the need for device changes or a larger incision. As shown and described herein, a single device can provide clamping from tips that extend parallel one another, each of which has features such as flat sections, saline ports, and electrical output capability.

FIG. 1 depicts a system according to a first embodiment. As shown in FIG. 1, a handheld device 100 includes a handle 102 and an insertion portion 104. The insertion portion 104 extends from a proximal end 106 near the handle 102 to a distal end 108 configured to provide a therapeutic effect such as sealing or clamping to the patient.

At the distal end 108, a housing 110 defines a slot 112 in which a pair of tips 114A, 114B are arranged. In FIG. 1, the handle 102 and the tips 114A are both arranged in a "closed" position (that is, with the tips 114A and 114B adjacent to one another in the center of the slot 112. As shown in FIG. 1, handle 102 can be manipulated to move the tips 114A and 114B relative to one another within the slot 112. That is, at one extreme of the range of movement of the handle 102 (and as shown in FIG. 1) the tips 114A, 114B are centered and pressed up against one another, while at the opposite extreme of the range of movement of the handle 102, the tips 114A and 114B are arranged apart from one another within the slot 112.

Handle 102 is ergonomically designed as a handle so that an operator can easily exert a large amount of force thereupon. The junction 116 between the handle 102 and insertion portion 104 as shown in FIG. 1 includes a spring that biases the device 100 such that the tips 114A and 114B are pushed apart. Junction 116 also includes substantial, sturdy components to facilitate the application of significant clamping force between the tips 114A and 114B by using the handle 102 in opposition to the spring at junction 116. It should be understood that in alternative embodiments, other junctions 116 could be used, such as those that provide ratcheting or locking mechanisms in the closed position, force assist through mechanical mechanisms (such as pulleys or gears), force assist through electronic mechanisms (such as an electronic motor).

In use, an operator of the device 100 inserts the distal end 108 towards a target area for treatment. The user can then manipulate the handle 102 relative to the insertion portion 104 to adjust the distance between the tips 114A and 114B. In this way, the user can provide clamping to a target at the distal end 108, such as a large vessel.

Although not shown in FIG. 1, a fluid supply can be coupled to the device to provide fluid to the tips 114A and 114B via the insertion portion 104. An electrical controller can be coupled to a power supply and configured to provide electrical power to each of the pair of tips 114A, 114B as well. A mechanical controller can be used to move the pair of tips relative to one another between a closed configuration and an open configuration, as described in more detail below with respect to FIGS. 2 and 3.

As described in more detail below, in addition to clamping the device 100 can also provide electrosurgical therapy such as small vessel poaching or sealing. These combined functions do not require removal of one tool for insertion of another, nor an incision large enough to hold two separate devices at the same time.

Figure 2:
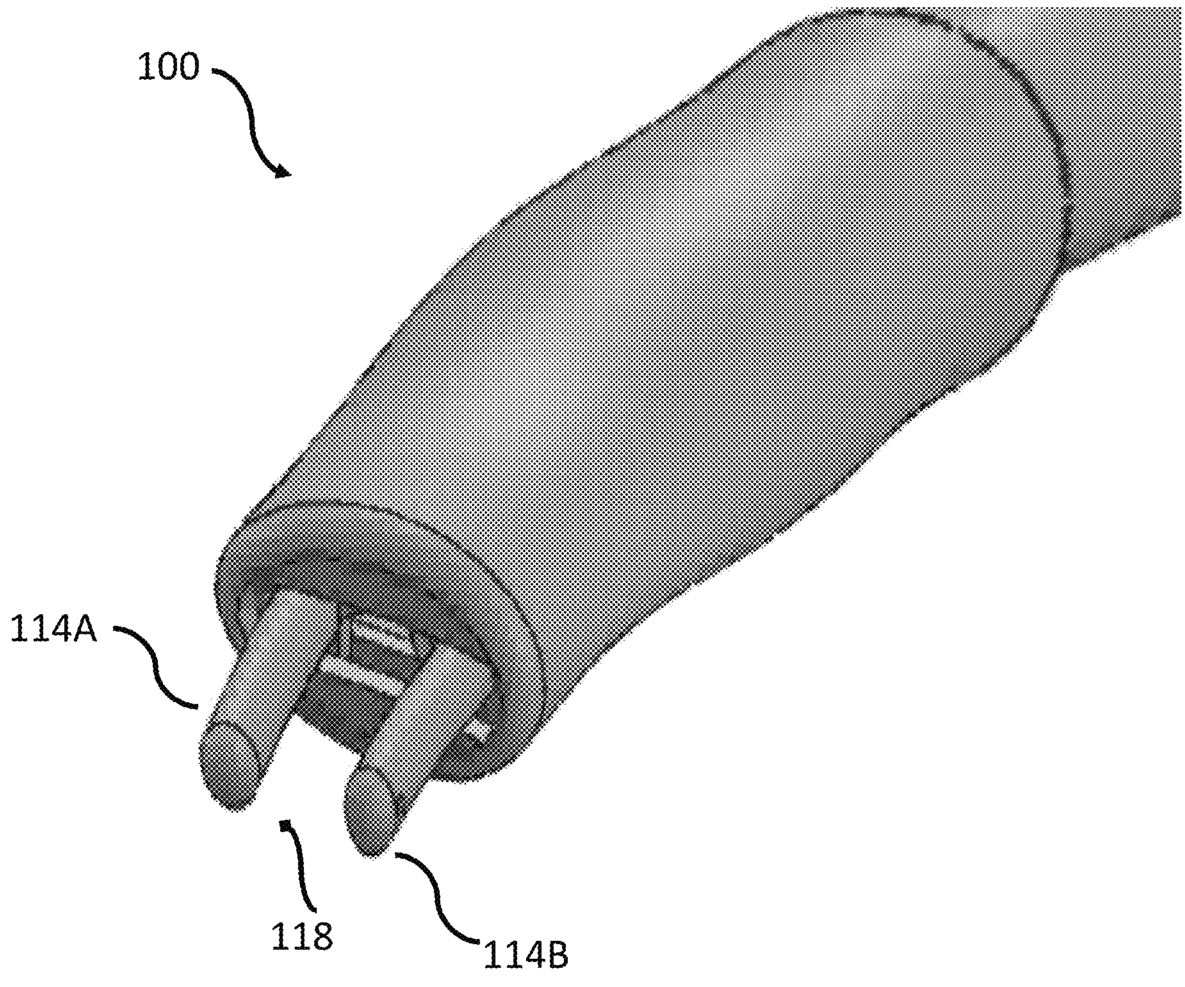
FIG. 2 is an alternate view of the device of FIG. 1 arranged with the tips in an open position.
Figure 3:
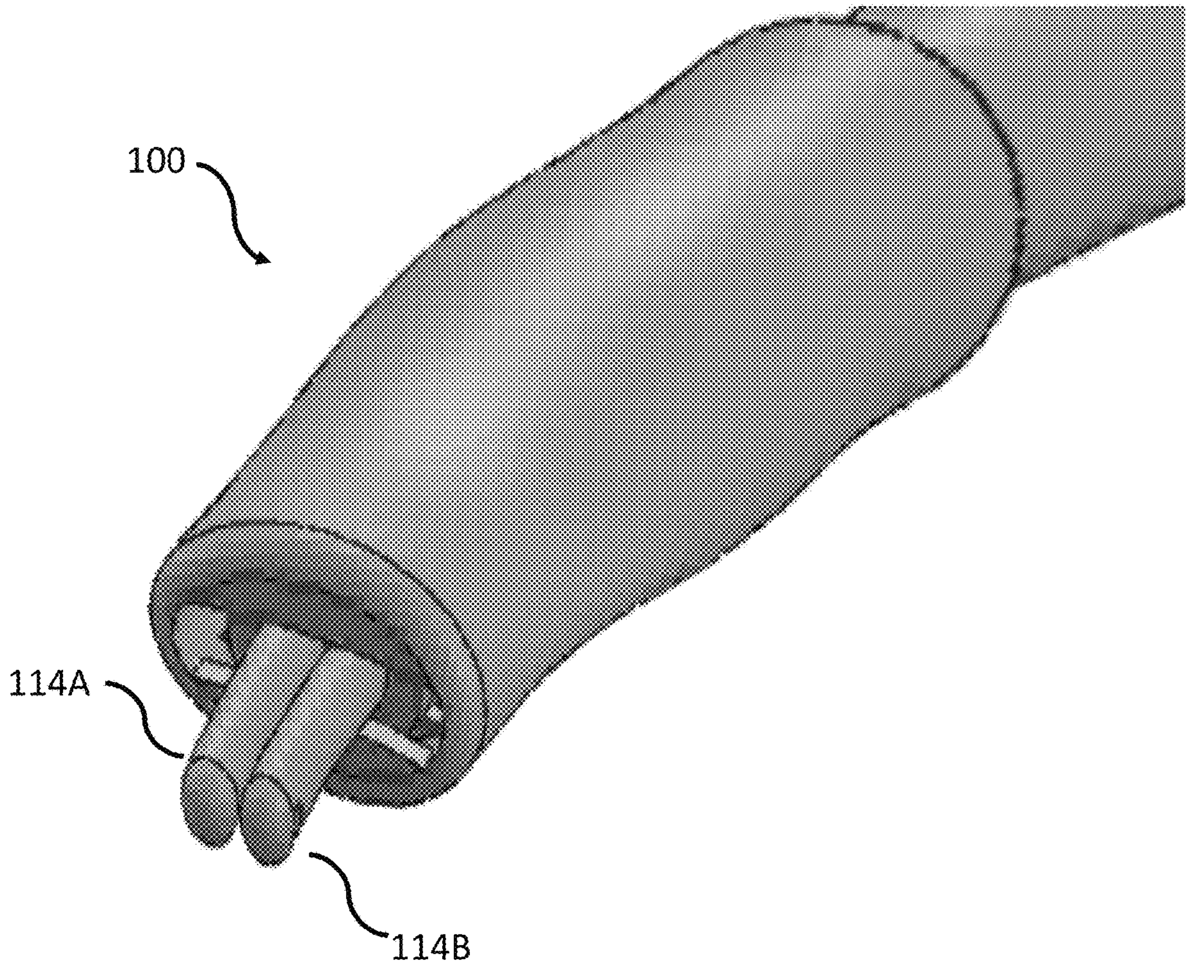
FIG. 3 is an alternate view of the device of FIGS. 1 and 2, arranged with the tips in a closed position.

FIG. 2 shows the device 100 of FIG. 1 in the open position, while FIG. 3 shows the device 100 of FIGS. 1 and 2 in the closed position.

As shown in FIG. 2, the tips 114A and 114B of the device 100 are separated from one another. A gap 118 is formed therebetween. In typical operation, as described above, a gap 118 can be created between the tips 114A and 114B by manipulating the handle 102 (FIG. 1) during positioning of the device 100. The gap 118 can advanced to a vessel or other structure that the user wishes to clamp. At that time, the handle 102 can be manipulated again to reduce or eliminate the gap 118 and clamp the structure.

As shown in the difference between FIGS. 2 and 3, the tips 114A and 114B remain parallel when gap 118 is opened and closed. The parallel tips 114A and 114B, rather than a non-parallel opening such as a scissor or a forceps, maintains a small size perpendicular to the tips 114A and 114B. In alternative embodiments, the tips 114A and 114B can be angled relative to one another, or can open in a non-parallel fashion, in order to provide specific types of clamping modes for specific applications.

Figure 4:
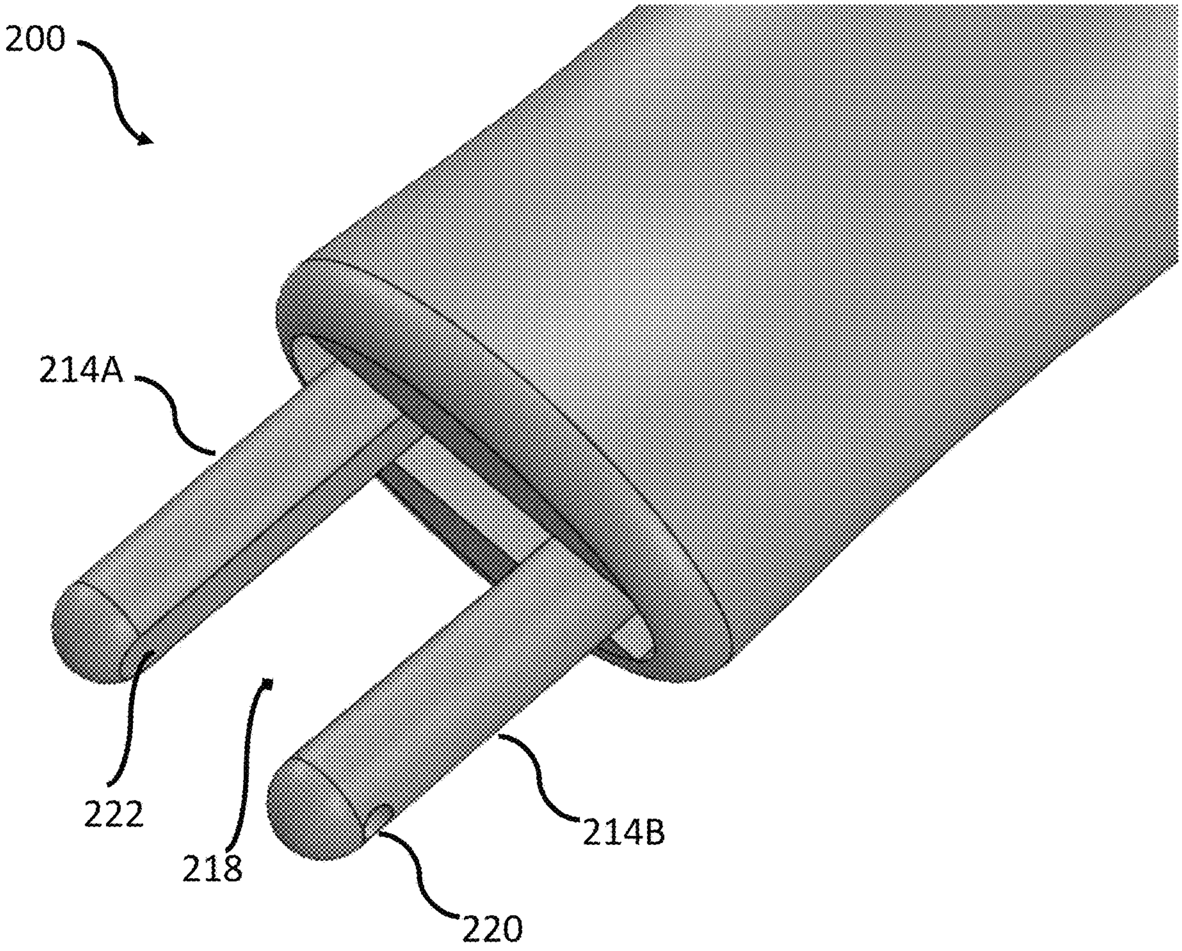
FIG. 4 is a detailed view of the tips of a system, including flats for clamping and ports for providing a liquid.

FIG. 4 shows a pair of tips 214A and 214B that include saline ports 220, within a device 200. Though not shown in the perspective of FIG. 4, a port 220 is also arranged on the opposite side of tip 214A, as a mirror image to the saline port 220 shown in tip 214B. Furthermore, though not shown in FIG. 4, the structures shown in FIG. 4 are coupled to a device similar to the device 100 of FIGS. 1-3, such that a user can manipulate the distance between the tips 214A and 214B as well as carry out saline distribution and electrical provision as described herein. Components, structures, and regions of device 200 are substantially similar to their corresponding components, structures, and regions described above with respect to FIG. 1, iterated by a factor of 100, with the differences described below. For brevity, description of these like parts is not repeated herein.

Saline ports 220 can bathe the region around tips 214A and 214B with a fluid such as saline, which is a good conductor of electricity and is not damaging to surrounding tissues and structures. The tips 214A and 214B themselves can provide electrical current sufficient to poach the bathed region. An operator can control the timing and amount of the saline dispensed from each of the ports 220 as well as the application of electrical signal. The electrical signal and saline provided by tips 214A and 214B can be sufficient to cause poaching of cut small vessels and tissues without being sufficient to cause injury or damage to larger structures that are adjacent thereto.

Tips 214A and 214B also include flats 222. In the embodiment shown in FIG. 4, flats 222 take the form of two parallel flat faces on the tips 214A and 214B. Flats 222 provide increased surface area for clamping structures within gap 218. When the handle or other control device is manipulated (see FIGS. 1-3) the gap 218 is closed or at least mostly closed, such that a structure is clamped between the flats 222.

Figure 5:
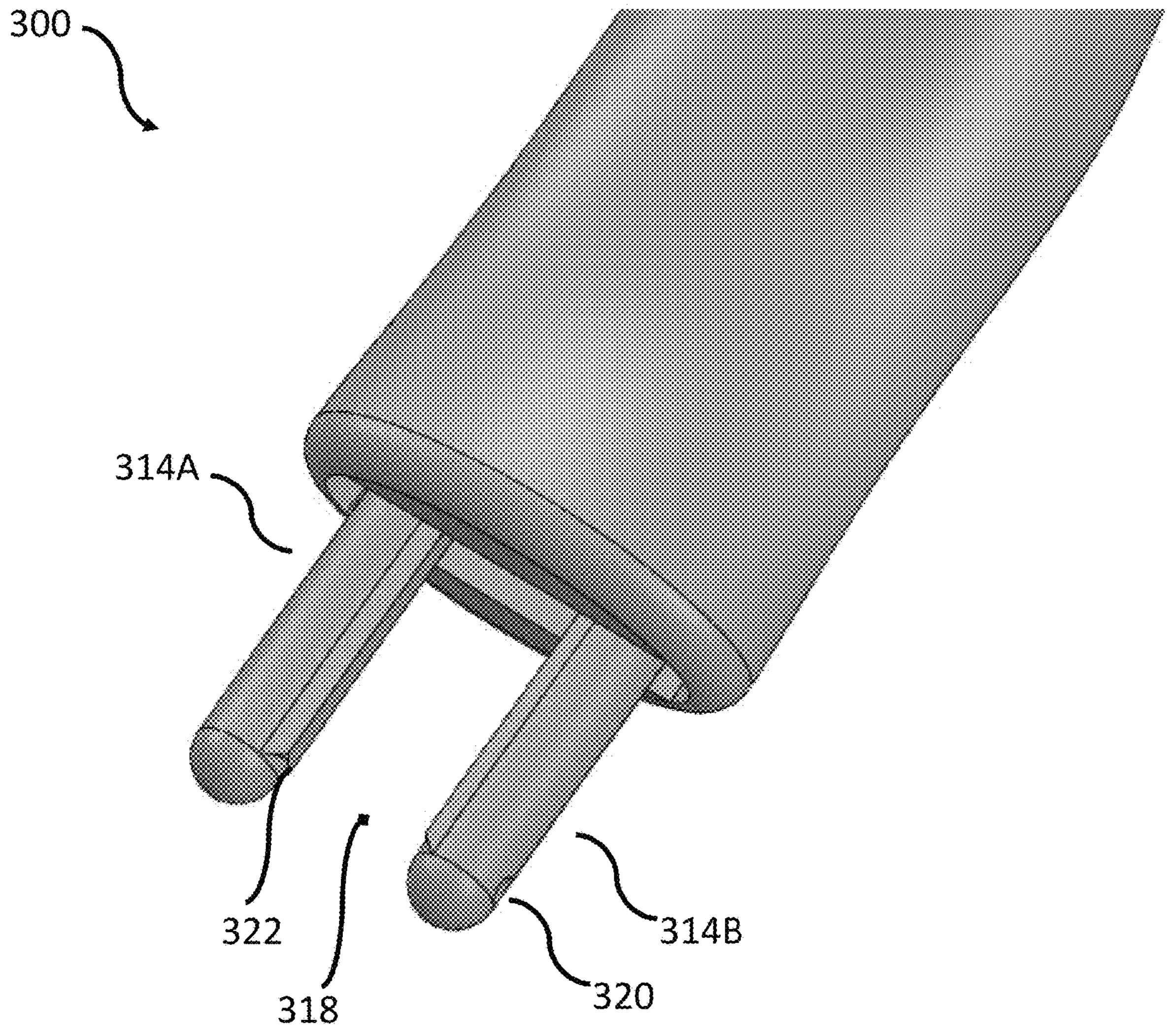
FIG. 5 is a detailed view of the tips of a system according to another embodiment, including flats that are built out from the cylindrical form factor of the tips.

FIG. 5 shows an alternative embodiment of a device 300, in which tips 314A and 314B include saline ports 320 and flats 322. Flats 322 of FIG. 5 differ from those shown in the embodiment of FIG. 4, in that they protrude from the otherwise cylindrical form factor of the tips 314A and 314B rather than being cut into that form factor. While described as "flats" throughout this application, structures such as those shown with respect to reference numbers 222 and 322 can be made in a variety of shapes that are not flat. For example, it may be beneficial in some embodiments to have gripping surfaces such as corrugations or protrusions that hold a structure to be clamped.

Figure 6A:
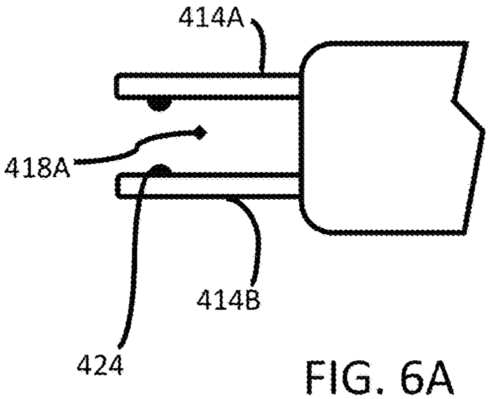
FIGS. 6A and 6B are schematic views of a system having two tips separated by two beads, according to an embodiment.
Figure 6B:
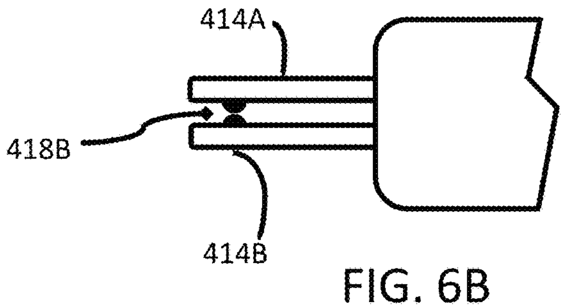
Figure 6C:
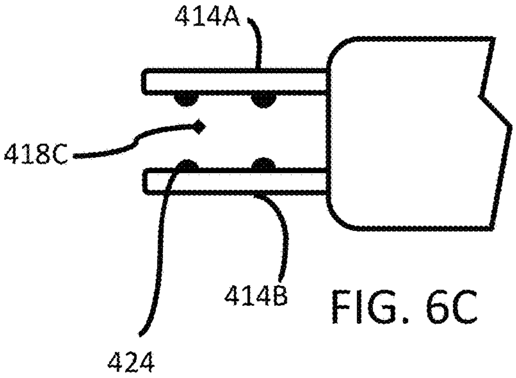
FIGS. 6C and 6D are schematic views of a system having two tips separated by four beads, according to an embodiment.
Figure 6D:
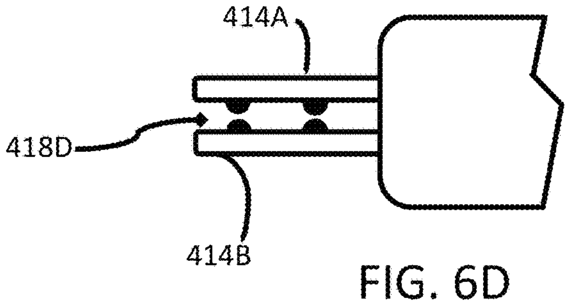

FIGS. 6A-6D show such gripping surfaces according to two embodiments. FIGS. 6A and 6B show the open and closed positions, respectively, of a device having a gripping bead 424 on each of the tips 414A and 414B. As shown by the difference between FIGS. 6A and 6B, the gap 418A in the open position is significantly larger than the gap 418B in the closed position. However, unlike other embodiments described above, there is always at least some gap between the tips 414A and 414B, enforced by the size of the beads 424. In embodiments the beads 424 can be ceramic or polymer, or some other electrically insulating material, so that current routed from one tip 414A to the other 414B does not pass through the beads 424 themselves. FIGS. 6C and 6D show an alternative embodiment that has multiple sets of beads 424 that prevent contact in the same manner.

Figure 7A:
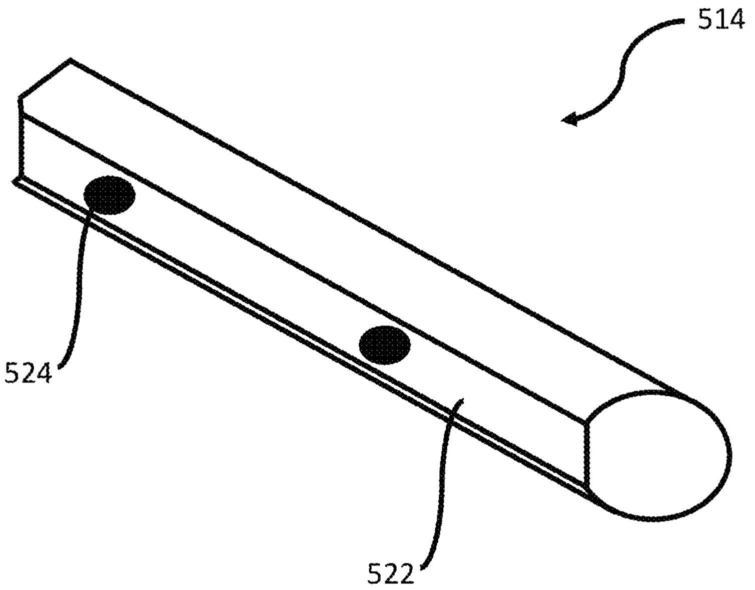
FIGS. 7A and 7B are front perspective and back perspective views, respectively, of the same tip, which includes two beads and a series of fluid dispensing ports having different geometries, according to an embodiment.
Figure 7B:
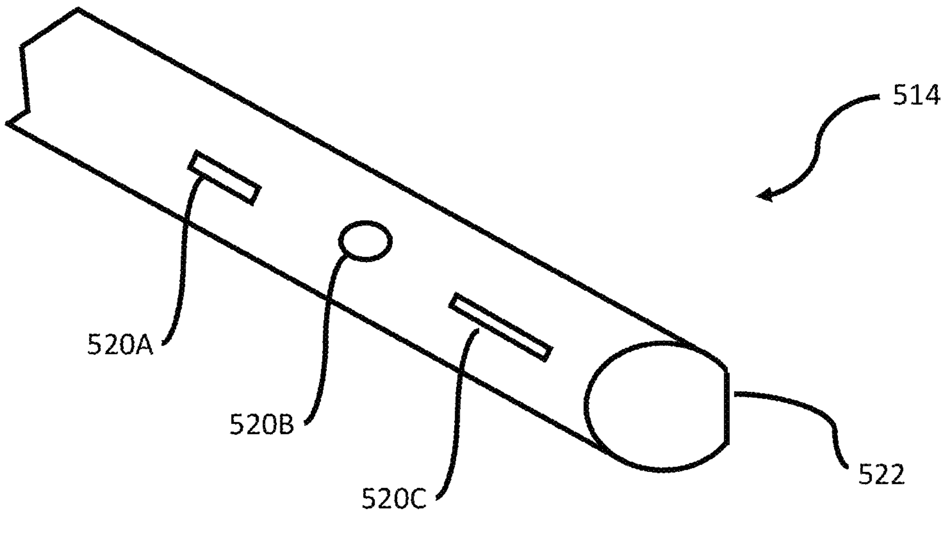

FIGS. 7A and 7B show a perspective inner view and a perspective outer view, respectively, of a tip 514. The tip of FIGS. 7A and 7B could be used in any of the above-described embodiments. In FIG. 7A, the beads 524 on flats 524 are shown in more detail. Similarly, in FIG. 7B, the saline ports 520A, 520B, and 520C are shown in more detail. While three saline ports (520A, 520B, and 520C) are shown in FIG. 7B, there may be only one port per tip (e.g., 514) in embodiments. Additionally, the size and shape of the ports 520A, 520B, and 520C varies, and it should be understood that depending on the desired amount and location of saline or other liquid to be dispensed, these ports could be modified as needed.

Figure 8A:
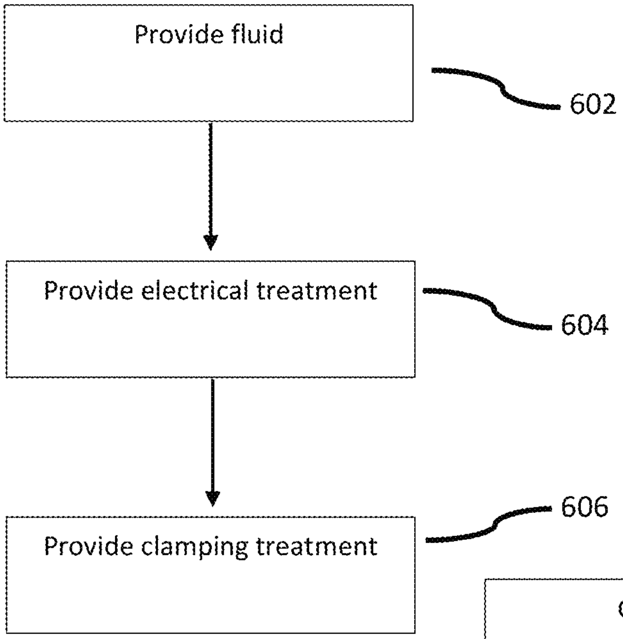
FIGS. 8A and 8B are methods for providing therapy using devices like those described herein according to embodiments.

FIG. 8A is a method for use of a device as described herein, according to an embodiment. At 602, a fluid is provided. The fluid can be provided at 602 by, for example, dispensing saline from a saline port. The fluid can be electrically conductive and non-harmful when in contact with a patient.

At 604, electrical treatment is provided. The electrical treatment can be, for example, providing electrical current from one tip to the other as described above, such that the current preferentially passes through the fluid dispensed at 602. The electrical treatment provided at 604 can provide poaching for healing or stabilizing of small vessels or tissue that is necessarily disrupted during a medical procedure.

At 606, clamping treatment is provided. As described herein with respect to FIGS. 1-3, the clamping treatment can be provided by bringing two parts of a device together around a larger vessel or other structure. The clamping can be provided at 606 by the same structures that provide the electrical treatment and the provision of saline at 604 and 602, respectively. In alternative embodiments, clamping can be provided at 606 before the saline and electrical treatments at 602 and 604.

Figure 8B:
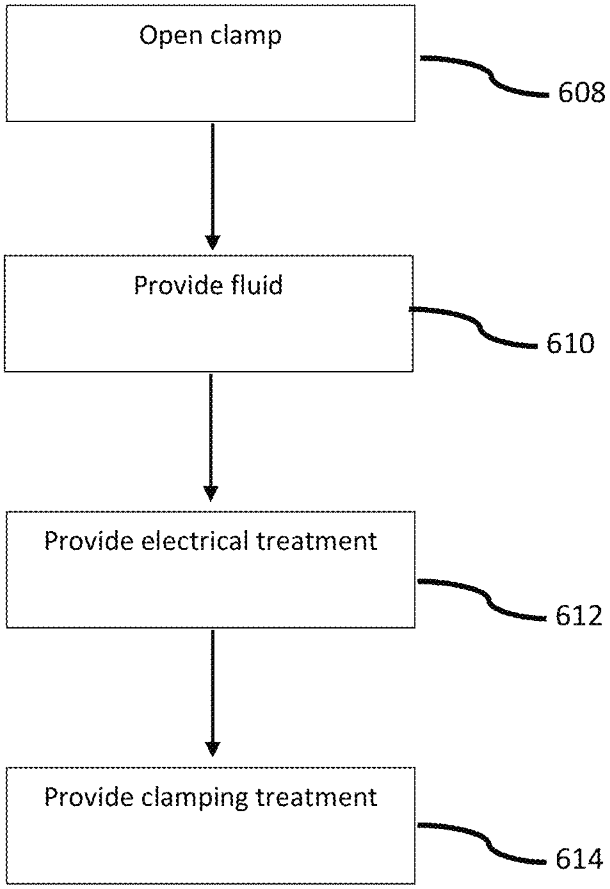

FIG. 8B shows another method, in which a clamp is opened at 608 (as described with respect to FIG. 1). The device can be positioned adjacent an area to be treated, and fluid provided at 610. After fluid has been provided to the area to be treated, electrical treatment can be provided at 612. Clamping treatment can also be provided at 614. As described previously, the clamping treatment at 614 and the electrical treatment at 612 can be provided by the same structures, and can be provided simultaneously, using a single device.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. For example, the level of clamping can be provided by a motor as described herein, which can be controlled electronically by hardware or software. Similarly, the electrical signal provided for electrical treatment can be provided using software and hardware componentry.

If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A tool comprising:

an elongated body extending between a proximal end and a distal end, the elongated body having a longitudinal axis;

a handle coupled to the elongated body at the proximal end, a junction between the handle and the elongated body, the junction including a spring configured to be compressed or extended in the direction of the longitudinal axis;

a pair of tips arranged at the distal end opposite the proximal end, each of the pair of tips having a corresponding fluid delivery aperture, a fluid supply coupled to each of the delivery apertures to provide a fluid thereto, an electrical controller configured to provide electrical power to each of the pair of tips, a mechanical controller configured to translate the pair of tips relative to one another between a closed configuration and an open configuration, wherein the pair of tips are parallel in the closed configuration and in the open configuration, and a housing at the distal end, the housing having a slot at a distal end of the housing, wherein the housing partially surrounds the pair of tips, wherein the pair of tips extend distally out of the slot but do not extend laterally beyond a lateral width of the housing in either the open configuration or the closed configuration, and wherein the pair of tips translate relative to one another within the slot, wherein the tool is configured such that the spring biases the pair of tips in the open configuration.

2. The tool of claim 1, wherein the handle includes the mechanical controller for moving the pair of tips.

3. The tool of claim 1, wherein each tip of the pair of tips extends parallel to the other tip of the pair of tips.

4. The tool of claim 3, wherein the mechanical controller is configured to maintain the pair of tips parallel to one another in both the open configuration and the closed configuration.

5. The tool of claim 1 wherein each tip of the pair of tips includes a flat portion.

6. The tool of claim 5, wherein the flat portions of the pair of tips are facing one another in both the open configuration and the closed configuration.

7. The tool of claim 6, wherein the delivery apertures are each arranged on the flat portions.

8. The tool of claim 5, wherein the flat portion of each of the pair of tips comprises a flange extending from each of the tips.

9. The tool of claim 1, wherein each of the pair of tips comprises at least one gripping bead.

10. A method for providing multiple treatment modes with a single device, the method comprising:

providing a device including:

an elongated body extending between a proximal end and a distal end, the elongated body having a longitudinal axis;

a handle coupled to the elongated body at the proximal end, a junction between the handle and the elongated body, the junction including a spring configured to be compressed or extended in the direction of the longitudinal axis;

a pair of tips arranged at the distal end opposite the proximal end, each of the pair of tips having a corresponding fluid delivery aperture, a fluid supply coupled to each of the delivery apertures to provide a fluid thereto, an electrical controller configured to provide electrical power to each of the pair of tips, a mechanical controller configured to translate the pair of tips relative to one another between a closed configuration and an open configuration, wherein the pair of tips are parallel to one another in the closed configuration and in the open configuration; and a housing at the distal end, the housing having a slot at a distal end of the housing, wherein the housing partially surrounds the pair of tips, wherein the pair of tips extend distally out of the slot but do not extend laterally beyond a lateral width of the housing in either the open configuration or the closed configuration, and wherein the pair of tips translate relative to one another within the slot, wherein the tool is configured such that the spring biases the pair of tips in the open configuration;

providing the fluid from the fluid supply at each of the delivery apertures;

providing an electrical treatment via the pair of tips to provide a sealing treatment function, and moving the handle relative to the elongated body to overcome the spring force so as to move the pair of tips from the open configuration to the closed configuration to provide a clamping treatment function.

11. The method of claim 10, wherein providing the fluid from the fluid supply occurs simultaneously with providing the electrical treatment.

12. The method of claim 11, wherein providing the fluid from the fluid supply, providing the electrical treatment, and providing the clamping treatment all occur simultaneously.

13. The method of claim 10, wherein the handle includes the mechanical controller for moving the pair of tips.

14. The method of claim 10, wherein each tip of the pair of tips extends parallel to the other tip of the pair of tips.

15. The method of claim 14, wherein the mechanical controller is configured to maintain the pair of tips parallel to one another in both the open configuration and the closed configuration.

16. The method of claim 10 wherein each tip of the pair of tips includes a flat portion.

17. The method of claim 16, wherein the flat portions of the pair of tips are facing one another in both the open configuration and the closed configuration.

18. The method of claim 17, wherein the delivery apertures are each arranged on the flat portions.

19. The method of claim 16, wherein the flat portion of each of the pair of tips comprises a flange extending from each of the tips.

20. The method of claim 10, wherein each of the pair of tips comprises at least one gripping bead.

* * * * *